United States Patent [19]

Adams et al.

[11] Patent Number: 4,491,566
[45] Date of Patent: Jan. 1, 1985

[54] AUTOMATIC $CO_2$ REMOVAL SYSTEM AND OPERATION THEREOF

[75] Inventors: Keith J. G. Adams, Knowle; Terrence P. Williams, Castle Bromwich; Norman T. Bolt, Iver; Qazi M. Siddique, London, all of England

[73] Assignee: British Gas Corporation, London, England

[21] Appl. No.: 368,831

[22] Filed: Apr. 15, 1982

[30] Foreign Application Priority Data

May 28, 1981 [GB] United Kingdom ............... 8116231

[51] Int. Cl.³ .................... B01D 53/34; G05D 7/00; G05D 9/00
[52] U.S. Cl. ................... 423/220; 423/232; 422/106; 422/109; 422/111; 422/115
[58] Field of Search ............ 423/220, 226, 228, 229, 423/232, 233; 422/105-116

[56] References Cited

U.S. PATENT DOCUMENTS

| | | | |
|---|---|---|---|
| 2,695,836 | 11/1954 | Gilmore | 423/232 X |
| 3,411,866 | 11/1968 | Jewell | 422/109 X |
| 3,958,943 | 5/1976 | Carmassi et al. | 423/228 X |
| 3,989,465 | 11/1976 | Onnen | 422/110 |
| 4,106,916 | 8/1978 | Tuckett et al. | 423/228 X |
| 4,210,627 | 7/1980 | Verloop et al. | 423/220 |
| 4,289,738 | 9/1981 | Pearce et al. | 423/220 X |
| 4,322,224 | 3/1982 | Roth | 422/111 X |

OTHER PUBLICATIONS

"Gas Processing Handbook", Hydrocarbon Processing, Apr. 1979, pp. 99 and 104–121.

*Primary Examiner*—Earl C. Thomas
*Attorney, Agent, or Firm*—Oblon, Fisher, Spivak, McClelland & Maier

[57] ABSTRACT

A system is described for removing $CO_2$ from the manufactured process gas in an SNG manufacturing plant, the system operating the hot carbonate process wherein hot potassium carbonate solution absorbs $CO_2$ from the process gas under pressure in an absorber column 1 and is regenerated by pressure reduction and steam stripping in a regenerator column 14 and a reboiler 17 before being returned to the absorber by a circulating pump 7. The system is completely automated and is controlled by a computer so that start-up, running and shut-down of the system is carried out automatically upon initiation by an operator, whereby the system is particularly suited for use in peak load SNG plants. For this purpose the system includes a solution make up tank 30, a solution storage tank 31, and a flushing water collection tank 32, preferably has all of its surfaces contacted by potassium carbonate solution made of stainless steel, and has sensors (F, L, T, P, AN, SG, and PH) and valve switches for transmitting information to the computer relating to the state of the system. The computer is programmed to operate the sequences of operation necessary to achieve the start-up, running and shut down of the system, operate loop controls on the solution levels in the absorber and regenerator columns, and on the rates of flow of solution to the absorber and of steam to the reboiler, and also to monitor the system parameters and to display data and signal alarm conditions.

38 Claims, 2 Drawing Figures

Fig. 2.

AUTOMATIC CO₂ REMOVAL SYSTEM AND OPERATION THEREOF

In the manufacture of fuel gas suitable for use as substitute natural gas (SNG), oil feed stocks are subjected to catalytic steam reforming to produce an intermediate gas comprising methane, carbon monoxide, carbon dioxide, and steam. The intermediate gas is further reacted to produce more methane from the carbon oxides and steam, but the final gas (hereinafter called process gas) contains appreciable excess and unwanted quantities of steam and carbon dioxide which must be removed before the gas can leave the plant for distribution. The manufacturing plant therefore includes a $CO_2$ removal system, and in general this operates by chemical absorption of the $CO_2$ by a suitable stripping liquid contacted with the process gas in an absorption column, the stripping liquid subsequently being regenerated by liberating the $CO_2$ before being returned to the column for re-use. One commonly used $CO_2$ removal system is based on the Hot Carbonate Process in which the stripping liquid used is potassium carbonate solution at a temperature near its atmospheric boiling point, regeneration of the solution being by pressure reduction and steam stripping.

The operation of an SNG manufacturing plant is complex and requires a number of highly trained operating staff, and we therefore consider that it would be advantageous to automate the operation and control of the plant as much as possible, particularly in the case of peak load plants, so that the operating staff required can be reduced to a minimum while at the same time ensuring safe, efficient, and reliable operation. As a step towards this the present invention is concerned with the automation of the $CO_2$ removal system of the plant using a computer based control. $CO_2$ removal systems are known in which there is at least some degree of automatic control of the system during normal running operation, but none include automatic control of the start-up and shut-down operations. For base load plants, which are run continuously for long periods, this may not matter too much, but for peak load plants which are operated often and for relatively short periods it is essential if full benefit is to be derived from automatic control of the normal running operation.

According to one aspect of the present invention, in a method of operating the $CO_2$ removal system in an SNG manufacturing plant and in which the process gas is passed through an absorber column in counter current to a stripping liquid which absorbs $CO_2$ from the process gas and which is then passed through a regenerator column at a lower pressure to liberate the $CO_2$ and through a steam heated reboiler to reheat the stripping liquid before it is pumped under pressure back to the absorber column, a computer is operated to run and control automatically sequences of operations for the start-up, running, and shut-down of the system, the start-up sequence comprising preheating the absorber and the regenerator columns and also the reboiler, supplying and measuring the rate of flow of steam to the reboiler and commencing loop control of the reboiler steam flow rate with a predetermined set point, commencing supply of stripping liquid at a predetermined minimum temperature to the regenerator column from a stripping liquid storage tank, measuring the level of stripping liquid in the regenerator column and commencing loop control of the regenerator liquid level with a predetermined set point, commencing transfer of stripping liquid from the regenerator column to the absorber column by operating a circulating pump when the regenerator liquid level reaches its set point, measuring the level of stripping liquid in the absorber column and commencing loop control of the absorber liquid level with a predetermined set point, commencing transfer of stripping liquid from the absorber column back to the regenerator column when the absorber liquid level approaches its set point, stopping the supply of stripping liquid from the storage tank to the regenerator column when the regenerator liquid level reaches a predetermined maximum value, measuring the rate of flow of the circulating stripping liquid and commencing loop control of the stripping liquid flow rate with a predetermined set point, the running sequence comprising continuing the loop controls and monitoring the concentration of the circulating stripping liquid, the regenerator liquid level loop control causing water or further stripping liquid from the storage tank, depending on whether the concentration of the circulating stripping liquid is above or below a predetermined set point, to be added to the regenerator column when the regenerator liquid level falls below its predetermined set point, and the shut down sequence comprising stopping the flow of process gas through the absorber column, maintaining circulation of the stripping liquid until regeneration of the liquid is complete and the liquid is ready to be stored, stopping the circulating pump, draining the stripping liquid from the absorber and regenerator columns and from the reboiler to the stripping liquid storage tank, supplying flushing water to the regenerator column, commencing transfer of flushing water from the regenerator column to the absorber column by operating the circulating pump when the regenerator liquid level reaches its predetermined set point, stopping the supply of flushing water to the regenerator column when flushing water is detected in the absorber column, commencing transfer of flushing water from the absorber column back to the regenerator column when the absorber liquid level approaches its predetermined set point, stopping the circulating pump, and draining the flushing water from the absorber and regenerator columns and from the reboiler to a flushing water storage tank.

According to another aspect of the present invention, an automated $CO_2$ removal system for use in an SNG manufacturing plant comprises an absorber column, a sensor for detecting the level of liquid in the column, means for feeding the process gas through the absorber column in countercurrent to a stripping liquid for absorbing $CO_2$ from the process gas, means including a flow control valve for feeding stripping liquid from the absorber column to a regenerator column for liberating $CO_2$ from the stripping liquid, a sensor for detecting the level of the liquid in the regenerator column, a steam heated reboiler for heating the stripping liquid, means for feeding steam to the reboiler and including a flow control valve and a flow rate sensor, a circulating pump for supplying liquid from the regenerator column under pressure to the absorber column via a flow control valve and a flow rate sensor, a storage tank for the stripping liquid, means including a flow control valve for feeding liquid from the storage tank to the regenerator column, a flushing water tank and means for connecting the flushing water tank to the regenerator column, and a computer which is arranged, in response to a program and inputs from the flow rate and liquid level sensors and from other sensors included in the system, to run and control automatically the sequence of operations for the start-up, running, and shut-down of the system as hereinbefore defined.

In the case of some $CO_2$ removal systems, such as that operating in Hot Carbonate Process, it is necessary as part of the start-up procedure to passivate any mild steel internals of the system. This can take as long as five days to complete and is obviously not compatible with a peak load plant where start-up should be as rapid as possible. Consequently, in the system in accordance with the invention the surfaces contacted by the stripping liquid are preferably stainless steel or some other material not requiring treatment prior to start-up of the system. The need for passivation or some other treatment is thereby avoided, and the start-up sequence programmed into the system enables the system to be brought on stream automatically from cold in two to three hours. The start-up operation is also improved by the preheating of the regenerator column prior to feeding the stripping liquid to it, and preferably this preheating is effected by feeding steam to the column under the control of the computer in response to the temperature measured at the top of the column as compared with a predetermined set temperature.

The shut-down of the system in accordance with the invention also takes less time than with existing systems, taking from three to four hours. One of the reasons for this is the inclusion in the system of a flushing water tank which is capable of storing all of the water used to flush the system in the shut down procedure. Consequently, when flushing is completed it is simply necessary to drain the flushing water to the storage tank instead of circulating the water until it is boiled away as in existing systems.

As with most computerised processes it is desirable that the operation of the system can be monitored and, if necessary, overridden by a human operator or controller. Preferably therefore, the computer monitors each stage of the start-up and shut-down sequences and also continually monitors the critical parameters and valve states via suitable sensors, transducers and transmitters, and displays information on a visual display unit VDU identifying the stage reached at any time, instructions which the operator may have to carry out, and any alarm condition which is detected. The system preferably includes data logging means which records system parameters at predetermined intervals during the running sequence and at any time on demand, and also records each alarm condition which is detected by the computer.

An example of an automated $CO_2$ removal system in accordance with the invention and its method of operation will now be described with reference to the accompanying drawings, in which.

Figure 1:
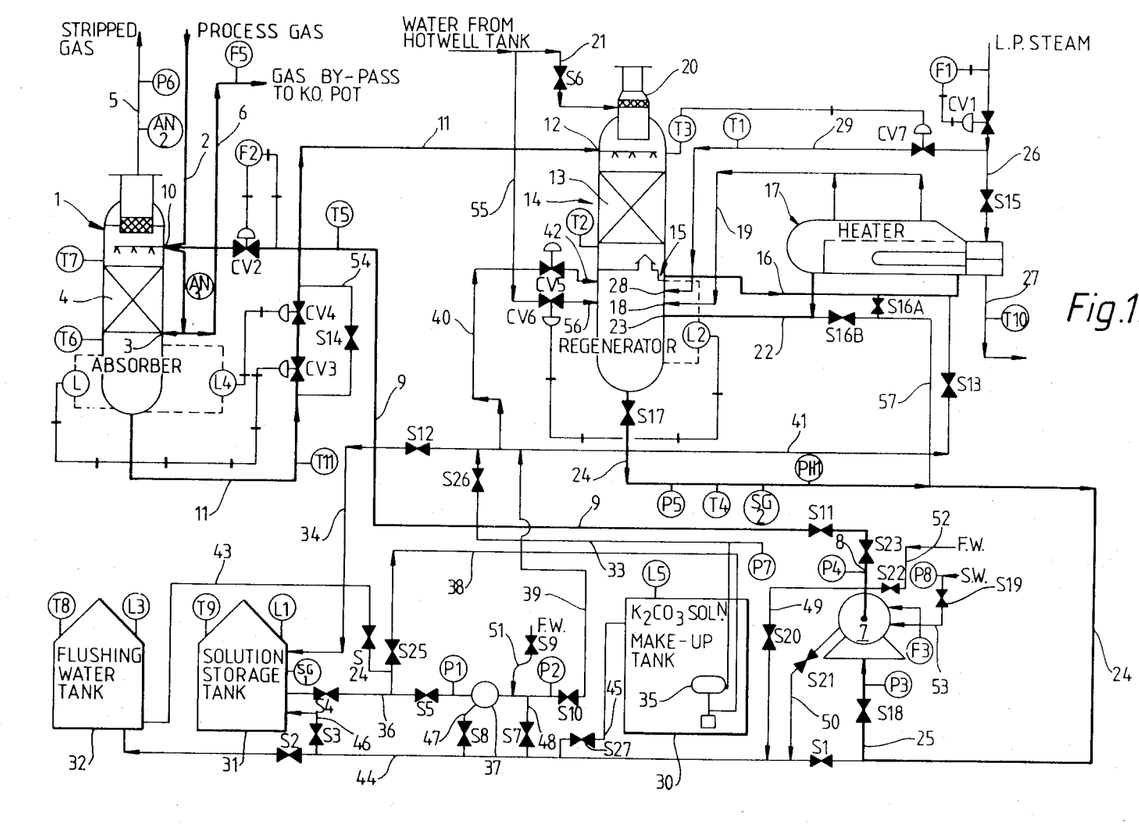
FIG. 1 is a schematic flow diagram of the system and indicating the locations of the various flow control valves and parameter measuring sensors of the system; and, FIG. 2 is a schematic block diagram illustrating the lay out of the computer based control system designed for controlling the operation of the plant shown in FIG. 1.
Figure 2:
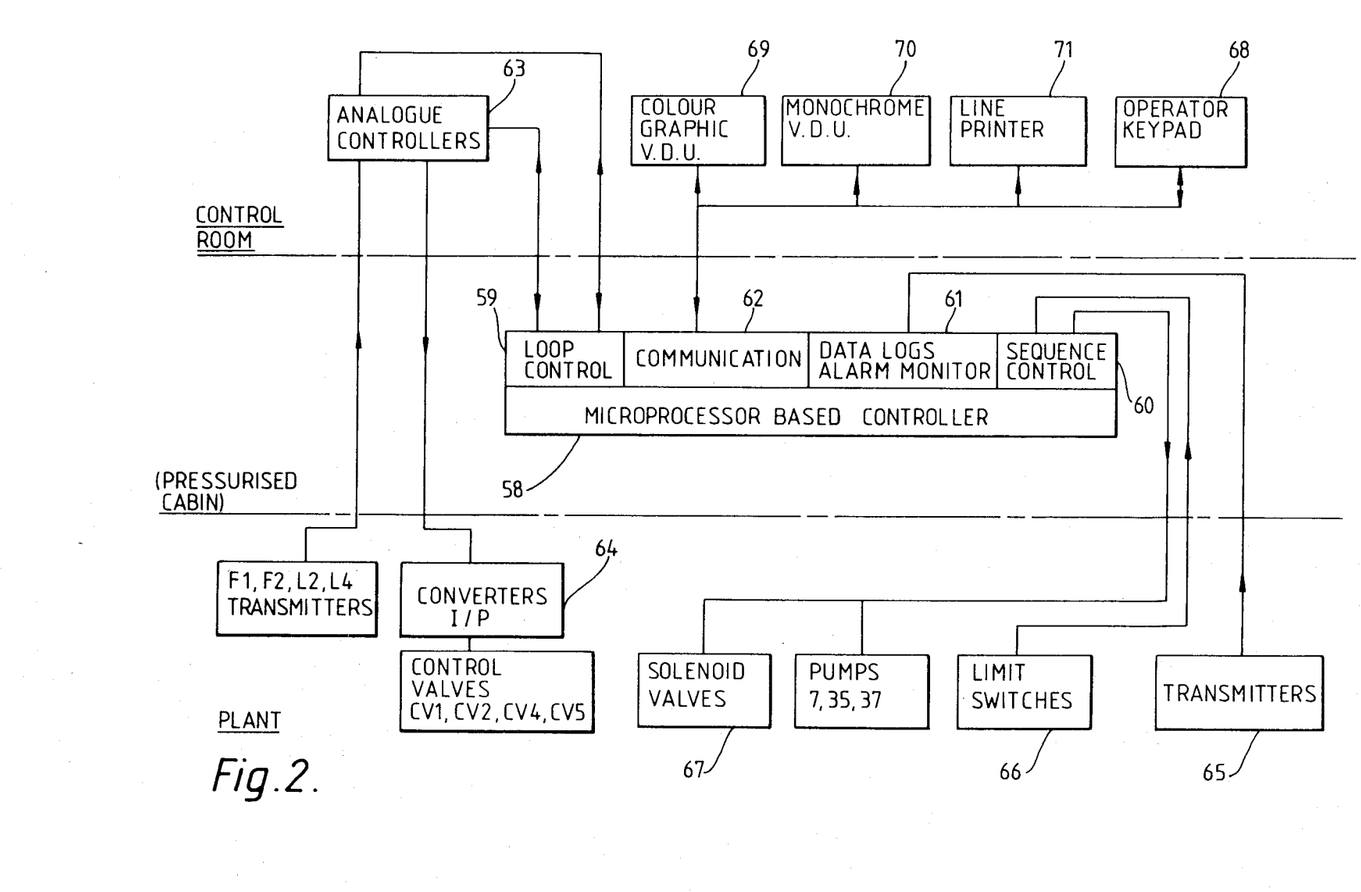

The system shown in the drawings is designed to operate the Hot Carbonate Process for stripping $CO_2$ from the manufactured process gas in an SNG plant by contacting the process gas at a pressure of about 320 psig and a temperature of about 120° C. with potassium carbonate solution at a similar temperature and pressure, $CO_2$ being absorbed by the solution to form potassium bicarbonate.

For this purpose the system comprises an absorber column 1 to which the process gas to be stripped is fed from a pipe 2 through an inlet opening into the column 1 at a position 3 below a stainless steel packing 4 in the column. The stripped gas leaves the column 1 through an outlet pipe 5 leading from the top of the column to knock out pots (not shown) for removing excess water vapour from the gas. If it is wished to bypass the column 1, the gas flowing through the pipe 2 can be diverted away from the inlet 3 and through a bypass pipe 6 leading directly to the knock out pots. The potassium carbonate solution is supplied under pressure to the absorber column 1 from a pump 7 through a pump outlet pipe 8 containing a block valve S23, a pipe 9 containing a block valve S11 and a variable flow control valve CV2, and an inlet opening into the column 1 at a position 10 above the packing 4 so that, in operation, the solution falls through the packing in countercurrent to the flow of process gas. The solution collects in the lower portion of the column 1 and an outlet pipe 11 leads from the base of the column through a slam shut control valve CV3 and a variable flow control valve CV4 to an inlet 12 above the packing 13 in a regenerator column 14.

The regenerator column 14 is operated at near atmospheric pressure, and the pressure reduction experienced by the solution which, in use, enters the column through the inlet 12 and which contains a mixture of potassium carbonate and potassium bicarbonate results in the evaporation of water and the flashing of carbon dioxide from the bicarbonate. The remainder of the solution falls through the packing 13, which is of stainless steel, to an intermediate position 15 from where it flows through a pipe 16 into an indirect steam heated reboiler 17. The heating of the solution in the reboiler 17 liberates further $CO_2$ and water vapour which is fed back into the regenerator column 14 at a position 18 via a pipe 19. The hot $CO_2$ and water vapour rise through the column 14, causing further liberation of $CO_2$ from the solution falling through the column, and the liberated $CO_2$ and water vapour leave the top of the column 14 through a demister section 20 supplied with water from a hot well tank (not shown) through a pipe 21 containing a block valve S6. The solution which is heated in the reboiler 17 is returned through a pipe 22 to the regenerator column 14 at a position 23, the regenerated potassium carbonate solution collecting at the bottom of the column from which it passes through a pipe 24 containing a block valve S17, and a pump inlet pipe 25 containing a block valve S18 to the pump 7 for recirculation to the absorber column 1.

Steam for heating the reboiler 17 is supplied to the reboiler through a pipe 26 containing a variable flow control valve CV1 and a block valve S15, and leaves the reboiler 17 through a pipe 27. Steam can also be supplied to the regenerator column 14 at a position 28 through a branch pipe 29 which contains a variable flow control valve CV7 and which leads from the steam supply pipe 26 between the valves CV1 and S15.

The system also comprises a solution make-up tank 30, a solution storage tank 31, and a flushing water tank 32. At the beginning of each gas making period a number of batches of 30% w/w strength potassium carbonate solution are made in the make-up tank 30 and are transferred to the solution storage tank 31 through a pipe 33 containing a block valve S26, and a pipe 34 containing a block valve S12 by means of a transfer pump 35 until the tank 31 is filled to the required level. At the required solution concentration crystallisation of the solution is likely to occur at ambient temperatures, and the make-up tank 30, the solution storage tank 31, and also the flushing water tank 32 are provided with heaters, for example steam coils, which are put into operation before the solution is prepared. An outlet pipe 36 from the solution storage tank 31 leads through block valves S4 and S5 to a pump 37 and has a branch pipe 38 leading from it upstream of the valve S5 through a further block valve S25 to the inlet of the pump 35 in the make-up tank 30. The outlet from the pump 37 is connected to a pipe 39 which leads through a block valve S10 to two further pipes 40 and 41. The pipe 40, which also communicates with the pipes 33 and 34 at the junction between the valves S12 and S26, leads into the regenerator column 14 at a position 42 through a variable flow control valve CV5, and the pipe 41 leads through a block valve S13 and joins the pipe 16 leading into the reboiler 17.

The flushing water tank 32 has an outlet pipe 43 which leads through a block valve S24 and joins the pipe 38 upstream from the block valve S25. The flushing water tank 32 also has an inlet pipe 44 which forms a main drainline which leads from the junction between the pipes 24 and 25 and which contains block valves S1 and S2. The make-up tank 30 and the solution storage tank 31 also communicate with the drainpipe 44, the former through a pipe 45 containing a block valve S27, and the latter through a pipe 46 containing a block valve S3. Also leading to the drainpipe 44 are pipes 47, 48, 49 and 50. The pipe 47 contains a block valve S8 and drains from the pump 37. The pipe 48 contains a block valve S7 and drains from the outlet pipe 39 from the pump 37. The pipe 49 contains a block valve S20 and drains from the outlet pipe 8 of the pump 7. The pipe 50 drains from the pump 7 itself and contains a block valve S21.

Provision is made for supplying flushing water to the pumps 37 and 7 through pipes 51 and 52 which respectively lead into the pump outlet pipes 39 and 8 and contain block valves S9 and S22. The pump 7 additionally receives a supply of sealing water through a pipe 53 containing a block valve S19.

In addition the system includes a pipe 54 containing a block valve S14 and bypassing the flow control valves CV3 and CV4 in the pipe 11; a branch pipe 55 leading from the hot well tank through a variable flow control valve CV6 to the lower part of the regenerator column 14 at position 56; and drainpipes communicating the solution flow pipes 16 and 22 respectively through block valves S16A and S16B to a pipe 57 leading into the main solution return pipe 24.

In addition to the packings 4 and 13 being made of stainless steel, the valve and pump parts contacted by potassium carbonate solution are also made of stainless steel. Furthermore, the absorber and regenerator columns, the reboiler, and at least the make-up and solution storage tanks will preferably be provided with stainless steel linings.

The operation of the plant shown in FIG. 1 is controlled (in a manner which will be described later) by a computer which is suitably programmed and which, in order to carry out its program, receives inputs from various different parts of the plant relating to various parameters of the process. For this purpose the plant is fitted with a number of sensors each of which measures a particular parameter of the process and is arranged to send a signal representative thereof to the computer, the sensor/transmitters being indicated in FIG. 1 at their approximate positions in the plant by circles containing identification letters and numbers. The sensors identified by the letter F measure flow rates; the sensors identified by the letter L are responsive to liquid levels in the associated vessels; the sensors identified by the letter T, such as sensors T4 and T5 shown in FIG. 1, are responsive to temperature, being constituted by thermocouples having a common cold junction mounted in the computer; the sensors identified by the letter P, such as sensors P5 and P8 shown in FIG. 1, measure pressure; the sensors identified by the letters AN measure the content of $CO_2$ in the gas flowing through the associated pipe; the sensors identified by the letters SG are responsive to the density of the potassium carbonate solution in the associated pipe or vessel; and the sensor connected to the pipe 24 and identified by the letters PH measures the pH value of the solution flowing through the pipe.

The block valves S1 to S27 are all pneumatically operated on/off valves actuated by solenoid valves in response to signals from the computer, each block valve having microswitches operative to send a signal to the computer when the valve reaches a fully open or closed state. The control valves CV1, CV2 and CV4 to CV7 are also operated by pneumatic actuators in response to modulating signals from the computer through suitable I/P converters. The control valves CV4 to CV7 are all fitted with limit switches which signal the computer when the valve is fully open or closed in the same way as the block valves. The valves CV1 and CV2 are proved open by signals from the flow rate sensors F1 and F2 respectively, but are provided with limit switches which signal the computer when the valves are closed. The control valve CV3 is an on/off slam shut valve provided with a limit switch for proving the valve closed only.

The general structure of the computer based control system of the plant is illustrated in FIG. 2. In the present example the computer, shown at 58, is a microprocessor based controller (th MPC 80 manufactured by Negretti Automation Ltd) capable of performing multi loop three term process control, wherein the control loops are controlled with 3-term feedback action sequence control, data logging and alarm monitoring, and communication, not only within itself but also with operator interface equipment and, if necessary, additional computers forming part of a larger distributed control system, these capabilities being represented respectively by the sections 59 to 62 of the computer 58. The computer is housed in a pressurised cabin local to the plant, and is wired, on one hand to the plant mounted hardware (i.e. the components which send or receive signals to or from the computer), and on the other hand to the operator's interface equipment mounted in a control room which may be remote from the plant.

As shown, the loop control section 59 receives signals from the flow rate sensors F1 and F2 and from the level sensors L2 and L4 via an analogue standby controller 63, and outputs electrical signals, again via the standby controller 63, which are converted by I/P converters 64 to pneumatic signals for operating the variable flow control valves CV1, CV2, CV4, CV5 and CV6. These valves are therefore controlled by the computer 58 in accordance with the input data from the sensors F1, F2, L2 and L4 and the stored data which is programmed into the computer and which determines the desired set points for the flow rates and liquid levels measured by the sensors F1, F2, L2 and L4. In the present example the control loops are programmed to perform in Direct Digital Control (DDC) with conventional three term feedback action, but as a relationship exists between the process gas throughput and the desired flow rates F1 and F2, the computer may also be programmed to perform a feed forward control loop in which the set points of the F1 and F2 control loops are modified according to measurements of the process gas throughput upstream from the absorber. Also, in the event of the $CO_2$ content of the gas leaving the top of the absorber column I, as measured by the analyser AN2, rising above a predetermined maximum, a local feedback control loop may be provided to modify the solution flow rate F2 and/or the reboiler steam flow rate F1 accordingly.

The analogue standby controller 63 is provided as a back up to the four critical control loops F1, F2, $L_2$ and L4 in case of computer failure. The controller can operate in any one of three modes, a computer mode in which the controller 63 receives and retransmits the control signals from the computer section 59, an automatic mode in which the computer is cut out and the controller operates as a conventional three term analogue controller, or a manual mode in which the computer is cut out and the output signal from the controller is controlled manually. In the computer mode, the controller 63 monitors the output signals from the computer and stores and updates the set points represented by the output signals. If the computer fails, the controller detects the failure and automatically switches to the local mode, operating with the fixed valve output values signalled immediately prior to failure. The controller 63 has a warning lamp for indicating when the computer signal has been cut out, at which the operator must switch the controller to either the manual or automatic mode. The set points adjusted when the controller is being operated in the manual or automatic mode, are monitored by the computer so that when the operator returns to the computer mode, the computer set points have been updated so that there should be a smooth transfer of control.

The data logging and alarm monitoring section 61 of the computer receives signals from all remaining plant sensors, represented jointly by the numeral 65 (i.e. all sensors except F1,F2, L2 and L4), and the sequence control section 60 receives the signals from the block and control valve limit switches, represented jointly by the numeral 66. The section 60 also sends operating signals to the plant pumps 7, 35 and 37, and to the solenoid valves, represented jointly by the numeral 67, which control the block valve actuators.

The operator's interface equipment, which is located in the control room along with the analogue standby controller 63, comprises an operator key pad 68, a colourgraphic visual display unit VDU 69, a monochrome visual display unit VDU 70, and a line printer 71 all linked to the communications section 62 of the computer, the communications section also being linked to the other sections of the computer.

The monochrome VDU is used to display sequence information on the state of the plant during operation and to display alarm conditions as they occur. In addition the sequence number and the step within the sequence, or control loop information is displayed at the bottom of the screen to enable the operator to see what position a sequence or control loop has reached at any particular time. All programming, editing, listing, and process adjustment is carried out with the aid of this VDU and either the operator key pad 68 or a further key pad (not shown).

The colourgraphic VDU is arranged to display any one of a number of mimic diagrams of the plant, bar graphs of the process control loops, or listings of plant parameters and alarms as instructed by the plant operator via the key pad 68. One of the plant mimic diagrams is an overall view of the plant showing all vessels, pumps, control valves, shut-off valves and interconnecting pipework; other diagrams showing individual sections of the plant in more detail and displaying relevant process parameters against the relevant vessels, pumps, valves and pipework. One of the main features displayed in these diagrams is the state of the block valves S. If a valve is proved closed, it is displayed in red; if it is proved open, it is displayed green; and when driving from one state to another it is displayed yellow. However, if a valve should be closed during a plant running state but it is not proved closed, the the valve will be displayed flashing red. Similarly, if a valve should be open when the plant is in a running state but it is not proved open, then the valve will be displayed flashing green. The state of each pump is also displayed to indicate whether it is running or not, red indicating that the pump is off and green indicating that it is on. The process control loop bar graph diagram indicates the set points as green arrows and the high/low alarm limits as red arrows. The measured value is displayed as a green vertical bar, while the control valve output signal (percentage output) is shown as a yellow vertical bar. The numerical values of the set point, the measured value, and the control valve output signal are displayed below each bargraph. If the measured value moves outside the high or low alarm limits, the vertical bar will change from green to red. In the diagrams which list the process parameters, any measurement which is an alarm condition will be indicated by a red flashing arrow at the right hand side of the parameter concerned. Once the alarm has been accepted by the operator (via an alarm accept button on the key pad 68) the flashing will stop but the red arrow will remain until the alarm condition has been rectified.

The line printer 71 is a receive only thermal printer and gives a hard copy print out of the process conditions either on demand or as programmed. During start up or shut down of the plant, each step of the sequence is logged together with the date and time. Any abnormal operation such as a valve failing to operate, a process parameter outside normal operating limits, or a specific input by the operator is automatically logged on the line printer. In addition, every hour or as demanded by the operator a print out of all the process parameters is given.

The operator key pad 68 is a push button panel which enables the operator to give the computer controller 58 certain commands, but the amount of information which the operator can access and modify through this key pad is strictly limited. It is intended that once the control loops are tuned satisfactorily then the operator will only be capable of modifying set points and will not be able to access the remainder of the control loop algorithm parameters such as PID (Proportional Integral Derivative) gains or alarm limits. These can only be changed, along with additional programming and editing of the data base and sequencing programs, using an additional key pad which is normally disconnected from the system.

In addition to the print button by which the operator may obtain a plant data log on demand from the line printer 71, and the alarm accept button, the key pad 68 has start up and shut down push buttons for initiating the start up and shut down sequences. The shut down switch is a latching type since the operator may call for a shut down at any time during the plant running sequence and a number of seconds may elapse before the state of the shut down switch is interrogated by the computer. The key pad also has run and hold buttons. A number of holding steps have been programmed into the start up and shut down sequences such that when the hold push button is latched in, the running program will wait at the next holding step it meets. The operator may hold the sequence indefinitely if wished. To continue the sequence the hold push button must be unlatched and the run button pressed. The pad 68 also has a series of buttons for activating and clearing the colourgraphic VDU 69, selecting the display required on the VDU 69, and means for raising or lowering the set point of any of the four critical control loops F1, F2, L2 and L4 if desired.

The sequences of operations controlled by the computer 58 during operation of the plant will now be described commencing with the start up sequence. The operator initiates the start up sequence by pressing the appropriate button on the key pad 68, and the first operations are a series of safe start checks. Some of these, such as the checking of the lubricating oil level in the pumps, are manual operations and the operator is instructed to carry these out by a display on the monochrome VDU 70. When these checks have been carried out the sequence continues with the automatic safe start checks. These consist of driving all the automatic block valves S1 to S27 to a closed position and proving them to be closed. In addition all the automatic control valves CV1 to CV7 are also driven closed and proved to be closed. The final check involves interrogating all inputs from plant temperature sensors (thermocouples) to ensure that there are no open circuits.

Once the safe start checks have been satisfied, an operation to heat the regenerator column 14 is automatically initiated. The regenerator column 14, the absorber column 1, and the reboiler 17 are all preheated prior to filling with the potassium carbonate solution in order to avoid possible solution crystallisation at low ambient temperatures. The regenerator heating operation opens the steam control valve CV7 and proves the valve open before putting the valve on the output of a temperature control loop having a set point of 70° C. and responsive to the temperature at the top of the column 14 as measured by the sensor T3. In this way the top of the regenerator packing 13 is controlled at a temperature of 70° C. via the steam flow to the bottom of the column at 28. Low pressure steam is supplied to the regenerator steam control valve CV7 by opening the control valve CV1 a preset amount and proving steam flow by the flow rate sensor F1. After a time delay of 30 seconds the temperature at T1 is sensed and, if greater than 30° C., proves steam flow to the regenerator column 13. A time delay of 10 minutes follows after which the temperature at the bottom of the regenerator packing 13 is checked by the sensor T2 to be greater than 30° C. Having proved that the regenerator packing 13 is being heated by a controlled steam flow, the absorber heating operation is begun.

The heating of the absorber packing 4 is carried out by the process gas, and in the present case the supply of process gas to the absorber column 1 is controlled manually, although it is anticipated that if the $CO_2$ removal plant were incorporated in a fully automated peak load SNG manufacturing plant, the supply of the process gas to the absorber would be automatic. The monochrome VDU displays the manual operations which the operator must carry out to commence the flow of process gas through the absorber, the system checking automatically that the process gas is heating the absorber packing 4 by proving the temperature as measured by the sensor T6 to be greater than 30° C. A 15 minute time delay follows, after which the temperature gradients across the absorber and regenerator packings 4 and 13 respectively are monitored. The temperature at the top of each packing, measured by the sensors T7 and T3 respectively, must be greater than 60° C. and the temperature gradient across each packing must be less than 10° C. before the sequence will continue. The final step of the absorber heating operation automatically drains any condensate which may have collected at the base of the absorber column 1. If the level sensor L4 indicates that condensate is present, the block valve S14 is opened and the condensate is driven under the pressure of the process gas in the column back into the regenerator column 14. As soon as the level sensor L4 registers zero, the block valve S14 is closed and proved closed, and the sequence moves on to drain condensate from the regenerator column. For this purpose the block valves S2, S1, S17, S16a, and S16b are opened and proved open sequentially to drain condensate under gravity from the column 14 into the flushing water tank 32. Low pressure steam from the inlet pipe 26 is then fed to the reboiler 17 by opening the block valve S15. Steam flow is proved by checking the temperature measured by the sensor T10 in the reboiler steam outlet pipe 27 to be greater than 30° C. Once it is proved that steam is heating the reboiler, the regenerator draining operation is completed by sequentially closing the valves S17, S16a, S16b, S1 and S2 and proving the valves closed.

The absorber and regenerator packing top temperatures and temperature gradients are then checked again as described earlier, and three safe start checks are carried out before the sequence commences filling the regenerator column 14 with the potassium carbonate solution. The first check monitors the solution level in the solution storage tank 31 by means of the level sensor L1 to ensure that sufficient solution is available to fill the plant. The second check ensures that the solution temperature, measured by sensor T9, is above 25° C. so that the solution will not crystallise during transfer, and the final check ensures that the concentration of the solution, determined by the sensor SG1, is greater than 28% w/w.

Once these checks have been completed satisfactorily, the block valves S7, S8 and S27 are sequentially opened and proved open before the valves S4 and S5 in the outlet pipe 36 from the solution storage tank 31 are opened to allow potassium carbonate solution to flow to the pump, the solution draining from the pump into the make-up tank 30. A time delay of 30 seconds is allowed for the pump to become properly primed, and the valves S7, S8 and S27 are then closed and proved closed. The inlet pressure, measured by sensor P1, to the pump 37 is checked to be greater than 1 psig before the pump 37 is started. The outlet pressure from the pump 37, measured by the sensor P2, is then checked and if greater than 30 psig the filling sequence continues by opening the valves S10 and S13 so that solution is pumped from the storage tank 31 firstly through the pipes 39 and 41 to the reboiler 17 and then into the regenerator column 14 through the pipe 22. The steam flow to the regenerator column is then stopped by closing the control valve CV7 and proving it closed, and DDC loop control of the steam flow rate to the reboiler 17 is then commenced with an initial set point of, in the present example, 3000 lb/hr and by measuring the flow rate F1. Solution is then also added to the regenerator column 14 through the inlet 42 by opening the control valve CV5 and commencing DDC loop control of the regenerator solution level measured by the sensor L2 with a predetermined set point. After a time delay of 5 minutes the regenerator level sensor L2 is checked for a reading greater than zero to prove that filling has begun.

When the regenerator level measured by L2 reaches the predetermined set point the absorber filling subsequence begins. The absorber column 1 is filled with potassium carbonate solution by the circulation pump 7 which pressurises solution drained from the base of the regenerator column 14 at approximately atmospheric pressure up to 360 psig at the inlet 10 to the absorber column 1, and the first part of the absorber filling operation deals with the priming of the circulation pump 7. Firstly the pump drain valves S20 and S21 are opened and proved open, and then solution is allowed to flow from the regenerator column 14 through the pipes 24 and 25 to the pump 7 by opening the valves S17 and S18. After 30 seconds the valve S19 is opened to supply high and low pressure seal water to the pump 7, the flow of seal water being proved by a pair of flow switches F3 before the valve S3 in the pipe 46 leading to the solution storage tank 31 is opened. After a further delay of 30 seconds, during which solution flows through the pump 7 and into the solution storage tank 31, the valves S20, S21 and S3 are closed sequentially and the inlet pressure to the circulation pump 7 is proved greater than 10 psig by the pressure sensor P3.

The pump 7 is then started and the valve S11 is opened simultaneously. However, before the valves S23 and CV2 are opened to allow the solution to be pumped through the pipe 9 to the absorber column 1, the pump outlet pressure is first proven greater than 200 psig by the pressure sensor P4 and is then proved to be above the absorber gas outlet pressure as measured by the pressure sensor P6. The control valve CV2 is opened and a time delay of 2 minutes is allowed following which the solution flow rate is checked to be greater than 3500 gall/hr by the flow sensor F2. The reboiler steam flow rate F1 is then increased to 10,000 lbs/hour. After a further 5 minutes the liquid level in the absorber is checked by the level sensor L4 to be greater than zero in order to prove that the absorber is filling, and DDC loop control of the absorber solution level, as measured by L4, is then commenced with a predetermined set point fixed for normal running conditions.

The control valve CV3 in the solution outlet pipe 11 from the absorber column is a pneumatically controlled slam shut valve which is installed as a local loop level control back up to the L4 loop control valve CV4. The valve CV3 is arranged to slam shut automatically if the solution level in the absorber falls below a predetermined minimum but will open automatically when the absorber solution level rises above the minimum value.

As the absorber solution level approaches the predetermined running set point level, the control valve CV4 begins to open to allow solution to transfer through the pipe 11 back to the regenerator column 14 under the pressure of the process gas in the absorber column 1. The returned solution is flashed to near atmospheric pressure at the top of the column 14 and falls through the regenerator packing 13 before passing under gravity through the pipe 16 to the reboiler 17 and then back through the pipe 22 to the regenerator column 14, thus completing the solution circulation route. The solution level L2 in the regenerator column 14 will now begin to rise since solution is still being pumped to the column 14 from the storage tank 31 via the reboiler 17 (the control valves CV5 being closed by the L2 loop control), and solution is also returning to the regenerator column from the absorber, the sequence holding this state until the required amount of solution has been transferred.

The valve S13 is then closed to stop the addition of further solution to the circulation route. The pump 37 is stopped and after a delay of 60 seconds the solution storage tank outlet valve S4 is closed. The valve S27 is then opened, followed by the drain valves S7 and S8 so that solution drains from the pump 37 and the pipes 36 and 39 through the pipe 45 to the make-up tank 30. The valve S12 is also opened to drain the pipes 40 and 41 through the pipe 34 into the solution storage tank 31. As soon as the outlet pressure of the pump 37 as measured by the sensor P2 is less than 20 psig the valves S10 and S5 are closed and flushing water is introduced to the pump through the pipe 51 by opening the valve S9. A 15 seconds period is allowed for flushing the pump 37, the flushing water draining away to the make up tank 30. The valves S5, S7, S8, S27 and S12 are then all closed to complete the pump solution draining and water flushing operation.

Water from the hot well tank is then introduced to the regenerator demister section 20 by opening the valve S6, and the final instruction in the automatic start up sequence puts the circulating solution flow rate, measured by F2, on DDC loop control with a set point of 12,000 gall/hr. The start up sequence is thus complete, with solution circulating in a route through the absorber column 1 back through the regenerator column 14 and the reboiler 17, and finally re-entering the absorber via the circulation pump 7. The absorber and regenerator solution levels are on DDC loop control with predetermined set points, and the reboiler steam flow rate and the solution circulation flow rate are also on DDC loop control with initial set points of 10,000 lb/hr and 12,000 gall/hr respectively.

On completion of the start up sequence, a running sequence is automatically initiated in which the solution concentration and total solution volume within the plant is maintained. Other sequences are carried out when the plant is running, such as valve monitoring, alarm monitoring, and data logging, and these sequences will be described later. The solution control sequence is required to maintain the set solution level in the regenerator column 14 (by means of the level loop control L2) and to maintain a constant solution concentration of 28% W/W as measured by the sensor SG2 in the pipe 24 leading from the base of the regenerator column 14, either solution or water being added to the column 14 as necessary by actuating either the control valve CV5 or the control valve CV6 depending on the circumstances.

If the solution level in the regenerator column 14 measured by L2 falls below its set point and the solution concentration measured by SG2 is not greater than 28% W/W, then a solution top up operation is commenced, the output signal from the regenerator level loop control L2 being switched to actuate the control valve CV5. The sequence then carries out safe start checks on the contents of the solution storage tank 31, checking that the temperature is greater than 25° C., that the solution level in the tank is greater than a predetermined minimum, and that the concentration of the solution in the tank is greater than 28% W/W. The level of solution measured by the sensor L5 in the make up tank 30 is then checked to be below its high alarm level before opening valves S4 and S25 to allow solution to flow from the storage tank 31 to the make up tank 30 for transfer to the regenerator column 14 by the pump 35. The make up tank pump 35 is used to transfer solution to the regenerator column since this pump has a lower discharge rate than the pump 37 and therefore does not require the control valve CV5 to be throttled back as much. It is thought that this will produce finer control of the regenerator liquid level L2 during the topping up operations. The level of solution in the make up tank 30 is then proved to be above its low alarm level and the pump 35 is started. When the pump discharge pressure, measured by the sensor P7, is greater than 25 psig the outlet valve S26 opens and solution is pumped into the regenerator column 14 via the control valve CV5. The sequence is held in this state with the control valve CV5 controlling the solution addition until the regenerator level L2 reaches the set point, or the solution concentration measured by sensor SG2 increases above 28% W/W, or the solution storage tank level measured by sensor L1 falls below its predetermined minimum. If any of these conditions occur the valve S26 is closed to stop the addition of solution, and the make up tank pump 35 is stopped. The inlet valves S4 and S25 are closed and the solution line 40 is drained back to the solution storage tank 31 by opening the valve S12 for a period of 30 seconds. If during the top up operation the make up tank high alarm level is reached, the valves S4 and S25 are closed until the level falls, and if the make up tank low alarm level is reached, the valve S26 is closed and the pump 35 stopped for one minute before continuing the sequence. The running sequence constantly returns to its initial conditional tests as to whether the regenerator solution level L2 is below the set point and whether the solution concentration at the regenerator outlet is greater than 28% W/W. If the level is low and the concentration is high, then a water top up operation is commenced.

If a water top up is required, the running sequence first checks whether the water level measured by the sensor L3 in the flushing water tank 32 is greater than a predetermined minimum, and if so then the stored flushing water is used to top up the regenerator column 14. The output signal from the regenerator level control loop L2 is again switched to actuate the control valve CV5 and an operation similar to that just described is carried out using the pump 35 to fill the regenerator column, but in this case transferring water from the flushing water tank 32 instead of solution from the solution storage tank 31. The flushing water temperature is first proved to be greater than 25° C. by the sensor T8, and then the sensor L5 is checked to ensure that the make up tank level is below its high alarm level before opening the valves S24 and S25. After checking that the make up tank level is above its low alarm level, the pump 35 is started and when the discharge pressure is proved by the sensor P7 to be greater than 25 psig the outlet valve S26 is opened to allow water to be pumped into the regenerator column via the control valve CV5. The sequence holds all valves in this state until the regenerator solution level L2 reaches its set point, or the solution concentration in the outlet pipe 24 falls below 28% W/W, or the flushing water tank level L3 falls below its predetermined minimum. If any of these conditions occur the top up operation is stopped by closing the valve S26 and stopping the pump 35. The valves S24 and S25 are then closed and the sequence continues from the initial conditional test of whether the regenerator solution level L2 is below the set point. As in the solution top up operation, the make up tank level sensor L5 is constantly monitored to ensure that neither extra-high nor extra-low levels are reached, thus preventing the tank from overflowing or the pump from running dry.

If during the running sequence it is determined that a water top up of the regenerator column is required, but the water level L3 in the flushing water tank 32 is below its predetermined minimum, then a water top up operation using water from the hot well tank is commenced. This simply involves switching the output signal from the regenerator level control loop L2 to actuate the control valve CV6 to allow water from the hot well tank into the column 14. The sequence remains in this state until either the regenerator level L2 reaches the set point or the solution concentration measured by the sensor SG2 falls below 28% W/W.

As will be appreciated, shut down of the plant may be required at any time and this is initiated by pressing the shut down button on the operator's key pad 68. However, if one of the regenerator top up operations described above is being carried out, the automatic shut down sequence will not commence until the operation is completed and it has been ensured that the pump 35 has been stopped and the various pipes involved have been drained of solution or water and isolated. As mentioned earlier, in the present example the process gas flows are controlled manually and the first operation of the shut down sequence is a command on the VDU 70 telling the operator to stop the supply of process gas to the column 1 and to bypass the process gas supply through the pipe 6. When this has been done the next operation in the sequence is to slowly increase the solution circulation flow rate to approximately 20,000 gall/hr. by further opening the control valve CV2 at a specific rate until the solution flow rate F2 approaches the desired value. The reboiler steam flow rate F1 is also increased to 12,000 lb/hr. by further opening the control valve CV1. The sequence is held in this state with solution being circulated and regenerated until the pH value of the solution measured by the sensor pH1 in the outlet pipe 24 from the regenerator column 14 is greater than 11. A pH value greater than 11 proves that the solution may be safely stored without risk of crystallisation. The valve S23 in the pump outlet pipe 8 is then closed and proved closed before the circulation pump 7 is stopped. The control valves CV1, CV2 and CV5/6 are then closed and the water flow to the regenerator demister section 20 is stopped by closing the valve S6. A delay of 60 seconds is provided to ensure that the pump 7 has stopped and that the pump inlet valve S18 is closed. The valves S20, S21, and S27 are then opened to drain solution in the pump back to the make up tank 30, and the seal water flow to the pump 7 is stopped by closing the valve S19, the sequence being held until the solution pressure measured by the sensor P4 at the pump outlet falls below 20 psig. The valves S20, S21 and S27 are then closed and the sequence progresses to a plant solution draining operation.

The valves S1 and S3 in the drainline 44 are opened and the regenerator outlet valve S17 is opened to allow solution to transfer under gravity from the regenerator column 14 to the solution storage tank 31. The absorber level control valve CV4 is opened fully to transfer solution under the absorber column pressure (approximately 310 psig) from the absorber column 1 to the regenerator column 14, the regenerator level L2 being held between set levels by on/off control of the valves S17 and S1. The sequence holds this state with solution being transferred from the absorber column to the regenerator column and being drained to the solution storage tank 31 until the absorber solution level L4 approaches the predetermined minimum level. Since the absorber column 1 must be fully drained of solution and the extra-low level control valve CV3 will slam shut below the predetermined minimum absorber level, the control valves CV3 and CV4 are bypassed at this stage of the sequence. Consequently the bypass valve S14 is opened and remains open until all solution is drained from the absorber column and the column has been partially depressurised. When the absorber pressure as measured by the sensor P6 falls below 200 psig, the valve S14 is closed and proved closed. The reboiler 17 is then drained of solution by opening the valves S16A and S16B, the valves S17, S1 and S3 remaining open. The sequence then waits for the regenerator solution level L2 to fall to zero, following which a 30 second time delay is provided for allowing solution the drain from the pipes 24 and 44 to the storage tank 31 before the sequence progresses to a water flushing operation.

In order to ensure that the flushing water storage tank 32 will be able to hold the full contents of the systm after it has been filled with flushing water, the tank 32 must first be emptied into the system. Consequently, if the level sensor L3 detects water in the flushing water tank 32, then a filling sequence using the pump 37 is commenced. After proving the temperature of the water in the tank 32 to be greater than 25° C. by the sensor T8, the valves S5, S7, S8, S24 and S27 are opened to prime the pump 37 for 30 seconds. The drain valves S7, S8 and S27 are then closed and the pump inlet pressure measured by the sensor P1 is proved greater than 1 psig before starting the pump 37. When the pump outlet pressure measured by the sensor P2 is above 30 psig the outlet valve S10 and the control valve CV5 are opened to allow flushing water to be pumped from the tank 32 into the regenerator column 14 until the tank is empty. The valve S10 is then closed and the pump 37 stopped, and after a delay of 30 seconds the pump water inlet valves S5 and S24 are also closed. The valves S16A and S16B, S17, S1, S3 and CV2 are then closed and the water flushing operation is continued using water from the hot well tank.

For this purpose the control valve CV6 is opened to allow water from the hot well tank into the regenerator column 14 via the pipe 55, and the sequence is held until the regenerator level L2 reaches its predetermined set point. The valves S17 and S18 are then opened to allow flushing water to flow from the column 14 to the circulation pump 7, and the pump is primed with the flushing water by opening the drain valves S20, S21, and S2 for a period of 30 seconds. The valve S19 is opened and the flow of seal water to the pump 7 is proved by means of the flow sensor F3. When the pump inlet pressure measured by P3 is greater than 10 psig, the pump 7 is started, and when the pump outlet pressure measured by the sensor P4 is greater than 200 psig and also greater than the absorber column pressure measured by P6, the pump outlet valve S23 is opened, the slam shut valve S11 having already opened simultaneously with the starting of the pump. The control valve CV2 in the pipe 9 leading to the absorber column 1 is opened to allow water to flow into the absorber column 1 at a rate of approximately 10,000 gall/hr., the rate being checked by the sensor F2. The absorber column 1 gradually fills with flushing water and as soon as a water level is detected in the absorber by the sensor L4 the control valve CV6 is closed to shut off the supply of water to the regenerator column 14. As the absorber fills, the slam shut valve CV3 opens when the water level reaches the predetermined minimum value, and the control valve CV4 opens when the water level reaches the normal running set point. On the opening of the valve CV4, the absorber column pressure forces flushing water from the absorber column 1 through the pipe 11 back into the regenerator column 14, thus completing water circulation. The pump outlet valve S23 is then closed and proved closed before the circulation pump 7 is stopped, the slam shut valve S11 closing at the deenergisation of the pump. The flow control valve CV2 is also closed and a time delay of 60 seconds is allowed to ensure that the pump 7 has stopped before the inlet valve S18 is closed. The pump is then drained by opening the valves S20, S21 and S2, and when the pump outlet pressure measured by P4 falls below 50 psig further flushing water is introduced to the pump 7 by opening the valve S22. The pump is flushed with water for 30 seconds before being isolated by closing the seal water valve S19, the flushing water valve S22, and the drain valves S20 and S21.

Water is then drained from the rest of the plant back into the flushing water storage tank 32, this operation commencing by opening the main drain valve S1, the valves S2 and S17 already being open, so that water then begins to drain from the base of the regenerator column 14 to the flushing water tank 32. The control valve CV4 is held open so that water transfers from the absorber column into the regenerator column, and at this stage the level of water L2 in the regenerator column 14 is maintained between set limits by opening and closing the valves S17 and S1. When the water level L4 in the absorber column 1 approaches the predetermined minimum value, the control valve CV4 is closed and the valves S17 and S1 are also closed. The absorber column 1 is then fully drained, using the residual pressure in the column, by opening the bypass valve S14 until the absorber level sensor L4 registers zero. The valve S14 is then closed and proved closed before final draining of the regenerator column 14 and the reboiler 17 is effected. For this purpose the valves S17, S1, S16A and S16B are opened until the regenerator level sensor L2 registers zero, whereupon the water draining operation is complete and the valves S16A, S16B, S17, S1 and S2 are closed. This terminates the automatic plant shut down.

As mentioned previously, in addition to the automatic start up, running, and shut down sequences, the computer 58 also carries out automatically a series of alarm monitoring sequences and a data logging sequence. In one of the alarm monitoring sequences the status of each of the block valves S1 to S27 is continually checked when the plant is in a running condition. If a valve is proved to be in an incorrect state then the relevant colourgraphic VDU mimic diagram will indicate the valve in a flashing colour and an alarm message will be displayed on the monochrome VDU as well as being logged by the line printer. In a second monitoring sequence conventional alarm scanning of critical plant parameters is carried out, and in the event of any parameter reaching an alarm level, an alarm message is displayed on the monochrome VDU and is logged by the line printer. In addition, the data view displays which can be called to the colourgraphic VDU will indicate the relevant alarm parameter and whether or not the alarm has been acknowledged via the alarm accept button on the operator's key pad. Finally, when the plant is being started up or shut down automatically, each step of the appropriate sequence is closely monitored and should a valve fail to open or close or a pressure or flow rate fail to be reached, an alarm message is displayed on the monochrome VDU and is logged by the line printer. In the event of an alarm occuring during the start up or shut down sequence, the program automatically holds the sequence to wait for operator correction. Any alarm detected by any of the alarm monitoring sequences, is also registered by an audible alarm signal which emanates from the operator's key pad 68 and which is silenced when the alarm accept button is pressed. The data logging sequence is programmed to be carried out automatically every hour, and prints a complete record of the plant parameters at the time. The sequence can be run at any other time to obtain similar logs simply by pressing the print push button on the operator's key pad 68.

As will be appreciated, a computerised $CO_2$ removal system has been described in which its operation is virtually completely automatic and in which the start up and shut down times are very considerably reduced compared with those taken in existing manual or semi-automatic systems, thus making the system particularly suitable for operation in peak load SNG plants.

We claim:

1. In a method of operating the $CO_2$ removal system in a substitute natural gas (SNG) manufacturing plant, in which the manufactured process gas is passed through an absorber column in countercurrent to a stripping liquid which absorbs $CO_2$ from the process gas and which is then passed through a regenerator column at a lower pressure to liberate the $CO_2$ and through a steam heated reboiler to reheat the stripping liquid before it is pumped under pressure back to the absorber column, the improvement comprising using a computer to run and control automatically sequences of operations for the start-up, running, and shut-down of the system, the start-up sequence comprising preheating the absorber and the regenerator columns and also the reboiler, supplying and measuring the rate of flow of steam to the reboiler and commencing loop control of the reboiler steam flow rate with a predetermined set point, commencing supply of stripping liquid at a predetermined minimum temperature to the regenerator column from a stripping liquid storage tank, measuring the level of stripping liquid in the regenerator column and commencing loop control of the regenerator liquid level with a predetermined set point, commencing transfer of stripping liquid from the regenerator column to the absorber column by operating a circulating pump when the regenerator liquid level reaches its set point, measuring the level of stripping liquid in the absorber column and commencing loop control of the absorber liquid level with a predetermined set point, commencing transfer of stripping liquid from the absorber column back to the regenerator column when the absorber liquid level approaches its set point, stopping the supply of stripping liquid from the storage tank to the regenerator column when the regenerator liquid level reaches a predetermined maximum value, measuring the rate of flow of the circulating stripping liquid and commencing loop control of the stripping liquid flow rate with a predetermined set point, the running sequence comprising continuing the loop controls and monitoring the concentration of the circulating stripping liquid, the regenerator liquid level loop control causing water or further stripping liquid from the storage tank, depending on whether the concentration of the circulating stripping liquid is above or below a predetermined set point, to be added to the regenerator column when the regenerator liquid level falls below its predetermined set point, and the shut down sequence comprising stopping the flow of process gas through the absorber column, maintaining circulation of the stripping liquid until regeneration of the liquid is complete and the liquid is ready to be stored, stopping the circulating pump, draining the stripping liquid from the absorber and regenerator columns and from the reboiler to the stripping liquid storage tank, supplying flushing water to the regenerator column, commencing transfer of flushing water from the regenerator column to the absorber column by operating the circulating pump when the regenerator liquid level reaches its predetermined set point, stopping the supply of flushing water to the regenerator column when flushing water is detected in the absorber column, commencing transfer of flushing water from the absorber column back to the regenerator column when the absorber liquid level approaches its predetermined set point, stopping the circulating pump, and draining the flushing water from the absorber and regenerator columns and from the reboiler to a flushing water storage tank.

2. A method according to claim 1, in which the stripping liquid is potassium carbonate solution.

3. A method according to claim 1 or claim 2, in which the absorber column is preheated and pressurised by passing the process gas through it.

4. A method according to claim 1, in which the regenerator column is preheated by steam supplied to the bottom of the column under the control of a temperature control loop having a predetermined set point and responsive to the temperature measured at the top of the column.

5. A method according to claim 1, in which the temperatures at the top and bottom of the absorber and regenerator columns are monitored and the computer prevents continuation of the start-up sequence until the column top temperatures are above the predetermined minimum value and the temperature gradients across the column packings are less than a predetermined maximum value.

6. A method according to claim 4, in which, following preheating of the absorber and regenerator columns, any condensate in the absorber column is detected and drained to the regenerator column, and condensate in the regenerator column is drained to the flushing water storage tank.

7. A method according to claim 1, in which during the start-up sequence stripping liquid is supplied to the regenerator column via the reboiler in addition to the loop controlled supply direct to the column.

8. A method according to claim 1, in which if during the running sequence the computer determines that water is to be added to the regenerator column, the water is added from the flushing water storage tank unless the level in the tank is below a predetermined minimum, in which case the water is added from a hot-well tank which serves to supply a demister at the top of the regenerator column.

9. A method according to claim 8, in which following initiation of the shut-down sequence, regeneration of the stripping liquid is carried out with increased flow rates for both the stripping liquid and the reboiler steam supply.

10. A method according to claim 9, in which regeneration is complete in the shut-down sequence when the pH value of the stripping liquid leaving the regenerator column is measured as greater than a predetermined value.

11. A method according to claims 8, 9 or 10, in which during the shut-down sequence the flushing water is supplied to the regenerator column from the flushing water storage tank until the tank is empty and thereafter from the hot-well tank.

12. A method according to claim 1, in which the control loops are controlled by the computer with 3-term feedback action.

13. A method according to claim 1, in which during the running sequence the process gas flow through the absorber column is monitored and the set points of the reboiler steam and the stripping liquid flow control loops are modified by a feed forward control loop in response to the process gas flow measurements.

14. A method according to claim 1, in which during the running sequence the $CO_2$ content of the process gas leaving the absorber column is monitored and is used to control a feedback loop to modify the stripping liquid flow rate and/or the reboiler steam flow rate if the $CO_2$ content rises above a predetermined maximum.

15. A method according to claim 1, in which the computer monitors each stage of the start-up and shut-down sequences and if a fault is detected an alarm is initiated and the sequence is automatically held pending operator correction.

16. A method according to claim 1, in which the computer monitors the system parameters and valve states and on detection of a fault an alarm is initiated.

17. A method according to claim 16, in which the system parameters are logged by an automatic printer at predetermined intervals.

18. An automated apparatus for removing $CO_2$ from the manufactured process gas in an SNG manufacturing plant, comprising an absorber column, a sensor for detecting the level of liquid in the column, means for feeding the process gas through the absorber column in countercurrent to a stripping liquid for absorbing $CO_2$ from the process gas, means including a flow control valve for feeding stripping liquid from the absorber column to a regenerator column for liberating $CO_2$ from the stripping liquid, a sensor for detecting the level of the liquid in the regenerator column, a steam heated reboiler for heating the stripping liquid, means for feeding steam to the reboiler and including a flow control valve and a flow rate sensor, a circulating pump for supplying liquid from the regenerator column under pressure to the absorber column via a flow control valve and a flow rate sensor, a storage tank for the stripping liquid, means including a pump and a flow control valve for feeding liquid from the storage tank to the regenerator column, a flushing water tank and means for connecting the flushing water tank to the regenerator column, and a computer which is arranged in response to a program and inputs from at least the flow rate and liquid level sensors, to run and control automatically the sequences of operations for the start-up, running, and shut-down of the apparatus, wherein the manufactured process gas is passed through said absorber column in countercurrent to said stripping liquid which absorbs $CO_2$ from the process gas and which is then passed through said regenerator column at a lower pressure to liberate the $CO_2$ and through said steam heated reboiler to reheat the stripping liquid before it is pumped under pressure back to the absorber column, said computer running and controlling automatically the start-up in a sequence comprising preheating the absorber and the regenerator columns and also the reboiler, supplying and measuring the rate of flow of steam to the reboiler and commencing loop control of the reboiler steam flow rate with a predetermined set point, commencing supply of stripping liquid at a predetermined minimum temperature to the regenerator column from a stripping liquid storage tank, measuring the level of stripping liquid in the regenerator column and commencing loop control of the regenerator liquid level with a predetermined set point, commencing transfer of stripping liquid from the regenerator column to the absorber column by operating a circulating pump when the regenerator liquid level reaches its set point, measuring the level of stripping liquid in the absorber column and commencing loop control of the absorber liquid level with a predetermined set point, commencing transfer of stripping liquid from the absorber column back to the regenerator column when the absorber liquid level approaches its set point, stopping the supply of stripping liquid from the storage tank to the regenerator column when the regenerator liquid level reaches a predetermined maximum value, measuring the rate of flow of the circulating stripping liquid and commencing loop control of the stripping liquid flow rate with a predetermined set point, the running sequence comprising continuing the loop controls and monitoring the concentration of the circulating stripping liquid, the regenerator liquid level loop control causing water or further stripping liquid from the storage tank, depending on whether the concentration of the circulating stripping liquid is above or below a predetermined set point, to be added to the regenerator column when the regenerator liquid level falls below its predetermined set point, and the shut down sequence comprising stopping the flow of process gas through the absorber column, maintaining circulation of the stripping liquid until regeneration of the liquid is complete and the liquid is ready to be stored, stopping the circulating pump, draining the stripping liquid from the absorber and regenerator columns and from the reboiler to the stripping liquid storage tank, supplying flushing water to the regenerator column, commencing transfer of flushing water from the regenerator column to the absorber column by operating the circulating pump when the regenerator liquid level reaches its predetermined set point, stopping the supply of flushing water to the regenerator column when flushing water is detected in the absorber column, commencing transfer of flushing water from the absorber column back to the regenerator column when the absorber liquid level approaches its predetermined set point, stopping the circulating pump, and draining the flushing water from the absorber and regenerator columns and from the reboiler to a flushing water storage.

19. An apparatus according to claim 18 for use in a peak load SNG plant, in which the surfaces contacted by the stripping liquid are stainless steel.

20. An apparatus according to claim 18 or claim 19, comprising means for feeding steam to the regenerator column for preheating the column in the start-up sequence, said means including a flow control valve which is controlled by the computer in response to the input from a temperature sensor at the top of the regenerator column.

21. An apparatus according to claim 20, in which, in addition to the input from the temperature sensor at the top of the regenerator column, the computer also receives inputs from a temperature sensor below the regenerator column packing and from temperature sensors above and below the absorber column packing.

22. An apparatus according to claim 18, in which the flushing water tank is coupled to the regenerator column via the pump and control valve by which stripping liquid is fed from the stripping liquid storage tank to the regenerator column.

23. An apparatus according to claim 18, in which the means for feeding liquid from the stripping liquid storage tank to the regenerator column comprises a main line which contains the flow control valve controlled by the regenerator liquid level control loop, and an auxiliary line which leads through the reboiler and which is opened when the regenerator column is being filled in the start-up sequence.

24. An apparatus according to claim 18, comprising a water tank for supplying water to a demister at the top of the regenerator column, and a line through which water is fed from the water tank to the lower part of the regenerator column when a control valve in the line is opened by the computer.

25. An apparatus according to claim 18, in which the means for feeding liquid from the absorber column to the regenerator column includes a further control valve which is responsive, during the running sequence, to a further absorber liquid level sensor to shut off the flow of stripping liquid from the absorber column if the liquid level in the column falls below a predetermined minimum.

26. An apparatus according to claim 18, in which the stripping liquid is potassium carbonate solution.

27. An apparatus according to claim 26, in which the system includes a make-up tank for preparing the required potassium carbonate solution, and a pump for transferring the solution to the stripping liquid storage tank.

28. An apparatus according to claim 27, in which the flushing water tank and the stripping liquid storage tank are each coupled to the make-up tank, and the make-up tank pump outlet is coupled to the regenerator column.

29. An apparatus according to claim 28, in which the computer is arranged to receive an input from a sensor fitted to the make-up tank for detecting the level of liquid in the tank.

30. An apparatus according to claim 26, including a density sensor and a pH sensor located between the bottom of the regenerator column and the circulating pump for providing inputs to the computer representing the concentration and crystallising temperature of the stripping liquid which is drawn from the regenerator column by the circulating pump.

31. An apparatus according to claim 18, in which the computer is arranged to receive inputs from sensors fitted to the stripping liquid storage tank for detecting the level, the temperature, and the concentration of the liquid in the tank.

32. An apparatus according to claim 18, in which the computer is arranged to receive inputs from sensors fitted to the flushing water tank for detecting the level and the temperature of the liquid in the tank.

33. An apparatus according to claim 18, in which the computer is arranged to receive inputs from pressure sensors fitted to the inlet and outlet of each of the pumps.

34. An apparatus according to claim 18, including sensors for providing inputs to the computer representing the concentration of $CO_2$ in the process gas entering and leaving the absorber column.

35. An apparatus according to claim 18, in which the control loop input and output signals to and from the computer are fed through an analogue stand-by controller which monitors the computer output signals and, in the event of computer failure, automatically takes over the control of the control loops using the set points held by the computer prior to failure.

36. An apparatus according to claim 18, in which each control valve includes means for sensing whether the valve is open or closed and for providing an input to the computer representing the valve state.

37. An apparatus according to claim 18 comprising a colourgraphic display unit on which the operator can select to display any one of a number of mimic diagrams illustrating parts of the system and their state or a list of the system parameters at that instant, any alarm condition being indicated by colour coding the relevant part or parameter.

38. An apparatus according to claim 37 including data logging means which records system parameters at predetermined intervals during the running sequence and at any time on demand, and also records each alarm condition which is detected by the computer.

* * * * *